(12) United States Patent
Cowley et al.

(10) Patent No.: US 8,594,806 B2
(45) Date of Patent: Nov. 26, 2013

(54) RECHARGING AND COMMUNICATION LEAD FOR AN IMPLANTABLE DEVICE

(75) Inventors: Anthony W. Cowley, Houston, TX (US); Robert J. Chilton, Austin, TX (US); Saadat Hussain, Houston, TX (US); David L. Thompson, Houston, TX (US)

(73) Assignee: Cyberonics, Inc., Houston, TX (US)

(*) Notice: Subject to any disclaimer, the term of this patent is extended or adjusted under 35 U.S.C. 154(b) by 240 days.

(21) Appl. No.: 12/772,010

(22) Filed: Apr. 30, 2010

(65) Prior Publication Data

US 2011/0270349 A1    Nov. 3, 2011

(51) Int. Cl.
*A61N 1/08* (2006.01)

(52) U.S. Cl.
USPC .................. 607/116; 607/60; 607/61; 607/30

(58) Field of Classification Search
USPC ........................ 607/30, 60, 61, 116
See application file for complete search history.

(56) References Cited

U.S. PATENT DOCUMENTS

| | | |
|---|---|---|
| 3,195,540 A | 7/1965 | Waller |
| 3,764,748 A | 10/1973 | Branch |
| 3,942,535 A | 3/1976 | Schulman |
| 3,952,750 A | 4/1976 | Mirowski |
| 4,014,346 A | 3/1977 | Brownlee |
| 4,082,097 A | 4/1978 | Mann |
| 4,102,344 A | 7/1978 | Conway |
| 4,134,408 A | 1/1979 | Brownlee |
| 4,143,661 A | 3/1979 | LaForge |
| 4,166,470 A | 9/1979 | Neumann |
| 4,172,459 A | 10/1979 | Hepp |
| 4,187,854 A | 2/1980 | Hepp et al. |
| 4,316,472 A | 2/1982 | Mirowski |
| 4,441,210 A | 4/1984 | Hochmair |
| 4,572,191 A | 2/1986 | Mirowski |
| 4,925,443 A | 5/1990 | Heilman |
| 5,167,229 A | 12/1992 | Peckham |
| 5,279,292 A | 1/1994 | Baumann |
| 5,290,227 A | 3/1994 | Pasque |
| 5,314,458 A | 5/1994 | Najafi |
| 5,350,413 A | 9/1994 | Miller |
| 5,405,367 A * | 4/1995 | Schulman et al. .............. 607/61 |
| 5,411,537 A | 5/1995 | Munshi |
| 5,522,865 A | 6/1996 | Schulman |
| 5,531,774 A | 7/1996 | Schulman |
| 5,545,191 A | 8/1996 | Mann |
| 5,569,156 A | 10/1996 | Mussivand |
| 5,569,307 A | 10/1996 | Schulman |
| 5,591,217 A | 1/1997 | Barreras |
| 5,603,726 A | 2/1997 | Schulman |
| 5,609,616 A | 3/1997 | Schulman |
| 5,630,836 A | 5/1997 | Prem |
| 5,676,162 A | 10/1997 | Larson |
| 5,676,651 A | 10/1997 | Larson |
| 5,690,693 A | 11/1997 | Wang |
| 5,693,091 A | 12/1997 | Larson |
| 5,702,430 A | 12/1997 | Larson |
| 5,702,431 A | 12/1997 | Wang |
| 5,704,891 A | 1/1998 | Mussivand |
| 5,713,939 A | 2/1998 | Nedungadi |
| 5,722,930 A | 3/1998 | Larson |
| 5,733,313 A | 3/1998 | Barreras |
| 5,741,316 A | 4/1998 | Chen |
| 5,749,909 A | 5/1998 | Schroeppel |
| 5,755,748 A | 5/1998 | Borza |
| 5,758,666 A | 6/1998 | Larson |
| 5,769,875 A | 6/1998 | Peckham |

(Continued)

*Primary Examiner* — Eric D. Bertram
(74) *Attorney, Agent, or Firm* — Cyberonics, Inc.

(57) ABSTRACT

A lead for an implantable device includes a flexible, implantable tether, electrically connectable to an implantable device, and a plurality of control elements, disposed along the tether. The control elements are electrically interconnectable to the implantable device and configured to transmit one of power and communication signals thereto.

22 Claims, 5 Drawing Sheets

(56) References Cited

U.S. PATENT DOCUMENTS

| | | | |
|---|---|---|---|
| 5,769,877 A | 6/1998 | Barreras | |
| 5,776,171 A | 7/1998 | Peckham | |
| 5,776,172 A | 7/1998 | Schulman | |
| 5,807,397 A | 9/1998 | Barreras | |
| 5,810,015 A | 9/1998 | Flaherty | |
| 5,814,095 A | 9/1998 | Muller | |
| 5,876,425 A | 3/1999 | Gord | |
| 5,879,375 A | 3/1999 | Larson | |
| 5,938,691 A | 8/1999 | Schulman | |
| 5,945,762 A | 8/1999 | Chen | |
| 5,948,006 A | 9/1999 | Mann | |
| 5,954,058 A | 9/1999 | Flaherty | |
| 5,954,758 A | 9/1999 | Peckham | |
| 5,991,664 A | 11/1999 | Seligman | |
| 5,991,665 A | 11/1999 | Wang | |
| 5,995,874 A | 11/1999 | Borza | |
| 5,999,848 A * | 12/1999 | Gord et al. | 607/2 |
| 6,026,328 A | 2/2000 | Peckham | |
| 6,047,214 A | 4/2000 | Mueller | |
| 6,052,624 A | 4/2000 | Mann | |
| 6,058,330 A | 5/2000 | Borza | |
| 6,061,596 A | 5/2000 | Richmond | |
| 6,067,474 A | 5/2000 | Schulman | |
| 6,067,991 A | 5/2000 | Forsell | |
| 6,070,103 A | 5/2000 | Ogden | |
| 6,088,619 A | 7/2000 | Hein | |
| 6,092,531 A | 7/2000 | Chen | |
| 6,099,495 A | 8/2000 | Kinghorn | |
| 6,115,636 A * | 9/2000 | Ryan | 607/60 |
| 6,141,588 A | 10/2000 | Cox | |
| 6,154,677 A | 11/2000 | Leysieffer | |
| 6,163,725 A | 12/2000 | Peckham | |
| 6,164,284 A | 12/2000 | Schulman | |
| 6,166,518 A | 12/2000 | Echarri | |
| 6,178,353 B1 | 1/2001 | Griffith | |
| 6,185,452 B1 | 2/2001 | Schulman | |
| 6,205,359 B1 | 3/2001 | Boveja | |
| 6,208,894 B1 | 3/2001 | Schulman | |
| 6,210,347 B1 | 4/2001 | Forsell | |
| 6,212,430 B1 | 4/2001 | Kung | |
| 6,212,431 B1 | 4/2001 | Hahn | |
| 6,227,204 B1 | 5/2001 | Baumann | |
| 6,240,316 B1 | 5/2001 | Richmond | |
| 6,240,318 B1 | 5/2001 | Phillips | |
| 6,246,911 B1 | 6/2001 | Seligman | |
| 6,263,247 B1 | 7/2001 | Mueller | |
| 6,266,567 B1 | 7/2001 | Ishikawa | |
| 6,269,266 B1 | 7/2001 | Leysieffer | |
| 6,272,382 B1 | 8/2001 | Faltys | |
| 6,275,737 B1 | 8/2001 | Mann | |
| 6,278,258 B1 | 8/2001 | Echarri | |
| 6,308,101 B1 | 10/2001 | Faltys | |
| 6,315,721 B2 | 11/2001 | Schulman | |
| 6,321,118 B1 | 11/2001 | Hahn | |
| 6,324,430 B1 | 11/2001 | Zarinetchi | |
| 6,324,431 B1 | 11/2001 | Zarinetchi | |
| 6,327,504 B1 | 12/2001 | Dolgin | |
| 6,331,744 B1 | 12/2001 | Chen | |
| 6,345,202 B2 | 2/2002 | Richmond | |
| 6,345,203 B1 | 2/2002 | Mueller | |
| 6,356,788 B2 | 3/2002 | Boveja | |
| 6,366,814 B1 | 4/2002 | Boveja | |
| 6,366,817 B1 | 4/2002 | Kung | |
| 6,368,592 B1 | 4/2002 | Colton | |
| 6,389,318 B1 | 5/2002 | Zarinetchi | |
| 6,392,386 B2 | 5/2002 | Schulmayr | |
| 6,393,325 B1 | 5/2002 | Mann | |
| 6,400,991 B1 | 6/2002 | Kung | |
| 6,415,186 B1 | 7/2002 | Chim | |
| 6,430,444 B1 | 8/2002 | Borza | |
| 6,442,434 B1 | 8/2002 | Zarinetchi | |
| 6,445,162 B1 | 9/2002 | Mukainakano | |
| 6,445,956 B1 | 9/2002 | Laird | |
| 6,450,173 B1 | 9/2002 | Forsell | |
| 6,450,946 B1 | 9/2002 | Forsell | |
| 6,453,198 B1 | 9/2002 | Torgerson | |
| 6,453,907 B1 | 9/2002 | Forsell | |
| 6,454,698 B1 | 9/2002 | Forsell | |
| 6,454,699 B1 | 9/2002 | Forsell | |
| 6,454,700 B1 | 9/2002 | Forsell | |
| 6,454,701 B1 | 9/2002 | Forsell | |
| 6,456,883 B1 | 9/2002 | Torgerson | |
| 6,460,543 B1 | 10/2002 | Forsell | |
| 6,461,292 B1 | 10/2002 | Forsell | |
| 6,461,293 B1 | 10/2002 | Forsell | |
| 6,463,935 B1 | 10/2002 | Forsell | |
| 6,464,628 B1 | 10/2002 | Forsell | |
| 6,464,655 B1 | 10/2002 | Shahinpoor | |
| 6,470,892 B1 | 10/2002 | Forsell | |
| 6,471,635 B1 | 10/2002 | Forsell | |
| 6,473,652 B1 | 10/2002 | Sarwal | |
| 6,475,136 B1 | 11/2002 | Forsell | |
| 6,477,425 B1 | 11/2002 | Nowick | |
| 6,482,145 B1 | 11/2002 | Forsell | |
| 6,496,733 B2 | 12/2002 | Zarinetchi | |
| 6,503,189 B1 | 1/2003 | Forsell | |
| 6,505,074 B2 | 1/2003 | Boveja | |
| 6,505,077 B1 | 1/2003 | Kast | |
| 6,516,227 B1 | 2/2003 | Meadows | |
| 6,525,512 B2 | 2/2003 | Wuzik | |
| 6,531,847 B1 | 3/2003 | Tsukamoto | |
| 6,533,733 B1 | 3/2003 | Ericson et al. | |
| 6,540,659 B1 | 4/2003 | Milbocker | |
| 6,542,777 B1 | 4/2003 | Griffith | |
| 6,551,345 B2 | 4/2003 | Vogel | |
| 6,553,263 B1 | 4/2003 | Meadows | |
| 6,554,762 B2 | 4/2003 | Leysieffer | |
| 6,564,102 B1 | 5/2003 | Boveja | |
| 6,564,807 B1 | 5/2003 | Schulman | |
| 6,565,503 B2 | 5/2003 | Leysieffer | |
| 6,570,363 B2 | 5/2003 | Boberschmidt | |
| 6,575,894 B2 | 6/2003 | Leysieffer | |
| 6,586,912 B1 | 7/2003 | Tsukamoto | |
| 6,587,724 B2 | 7/2003 | Mann | |
| 6,591,139 B2 | 7/2003 | Loftin | |
| 6,592,512 B2 | 7/2003 | Stöckert | |
| 6,609,032 B1 | 8/2003 | Woods | |
| 6,611,715 B1 | 8/2003 | Boveja | |
| 6,615,081 B1 | 9/2003 | Boveja | |
| 6,620,094 B2 | 9/2003 | Miller | |
| 6,622,049 B2 | 9/2003 | Penner | |
| 6,628,989 B1 | 9/2003 | Penner | |
| 6,629,923 B2 | 10/2003 | Leysieffer | |
| 6,631,296 B1 | 10/2003 | Parramon | |
| 6,654,638 B1 | 11/2003 | Sweeney | |
| 6,657,351 B2 | 12/2003 | Chen | |
| 6,662,052 B1 | 12/2003 | Sarwal | |
| 6,664,763 B2 | 12/2003 | Echarri | |
| 6,668,191 B1 | 12/2003 | Boveja | |
| 6,675,045 B2 | 1/2004 | Mass | |
| 6,678,561 B2 | 1/2004 | Forsell | |
| 6,695,885 B2 | 2/2004 | Schulman | |
| 6,697,674 B2 | 2/2004 | Leysieffer | |
| 6,709,385 B2 | 3/2004 | Forsell | |
| 6,718,210 B1 | 4/2004 | Peckham | |
| 6,726,678 B1 | 4/2004 | Nelson | |
| 6,731,986 B2 | 5/2004 | Mann | |
| 6,736,770 B2 | 5/2004 | Leysieffer | |
| 6,745,077 B1 | 6/2004 | Griffith | |
| 6,764,446 B2 | 7/2004 | Wolinsky | |
| 6,772,011 B2 | 8/2004 | Dolgin | |
| 6,807,445 B2 | 10/2004 | Baumann | |
| 6,810,289 B1 | 10/2004 | Shaquer | |
| 6,850,803 B1 | 2/2005 | Jimenez | |
| 6,856,838 B2 | 2/2005 | Parramon | |
| 6,875,180 B2 | 4/2005 | Weiner | |
| 6,879,859 B1 | 4/2005 | Boveja | |
| 6,891,353 B2 | 5/2005 | Tsukamoto | |
| 6,894,456 B2 | 5/2005 | Tsukamoto | |
| 6,895,280 B2 | 5/2005 | Meadows | |
| 6,901,290 B2 | 5/2005 | Foster | |
| 6,909,917 B2 | 6/2005 | Woods | |
| 6,915,165 B2 | 7/2005 | Forsell | |
| 6,937,894 B1 | 8/2005 | Isaac | |

(56) References Cited

U.S. PATENT DOCUMENTS

| | | |
|---|---|---|
| 6,949,929 B2 | 9/2005 | Gray |
| 6,954,674 B2 | 10/2005 | Connelly |
| 6,979,351 B2 | 12/2005 | Forsell |
| 7,001,427 B2 | 2/2006 | Aharoni |
| 7,003,350 B2 | 2/2006 | Denker |
| 7,003,353 B1 | 2/2006 | Parkhouse |
| 7,009,362 B2 | 3/2006 | Tsukamoto |
| 7,011,624 B2 | 3/2006 | Forsell |
| 7,016,738 B1 | 3/2006 | Karunasiri |
| 7,017,583 B2 | 3/2006 | Forsell |
| 7,024,248 B2 | 4/2006 | Penner |
| 7,054,691 B1 | 5/2006 | Kuzma |
| 7,062,330 B1 | 6/2006 | Boveja |
| 7,062,331 B2 | 6/2006 | Zarinetchi |
| 7,063,691 B2 | 6/2006 | Nelson |
| 7,076,304 B2 | 7/2006 | Thompson |
| 7,076,307 B2 | 7/2006 | Boveja |
| 7,079,901 B1 | 7/2006 | Loftin |
| 7,082,336 B2 | 7/2006 | Ransbury |
| 7,092,762 B1 | 8/2006 | Loftin |
| 7,107,103 B2 | 9/2006 | Schulman |
| 7,114,502 B2 | 10/2006 | Schulman |
| 7,120,992 B2 | 10/2006 | He |
| 7,123,013 B2 | 10/2006 | Gray |
| 7,123,966 B2 | 10/2006 | Deininger |
| 7,126,310 B1 | 10/2006 | Barron |
| 7,151,914 B2 | 12/2006 | Brewer |
| 7,155,291 B2 | 12/2006 | Zarinetchi |
| 7,167,756 B1 | 1/2007 | Torgerson |
| 7,171,273 B2 | 1/2007 | Shaquer |
| 7,177,690 B2 | 2/2007 | Woods |
| 7,177,691 B2 | 2/2007 | Meadows |
| 7,177,698 B2 | 2/2007 | Klosterman |
| 7,180,760 B2 | 2/2007 | Varrichio |
| 7,184,836 B1 | 2/2007 | Meadows |
| 7,191,007 B2 | 3/2007 | Desai |
| 7,191,012 B2 | 3/2007 | Boveja |
| 7,198,594 B2 | 4/2007 | Shahinpoor |
| 7,198,603 B2 | 4/2007 | Penner |
| 7,200,504 B1 | 4/2007 | Fister |
| 7,212,110 B1 | 5/2007 | Martin |
| 7,212,864 B2 | 5/2007 | Wahlstrand |
| 7,225,032 B2 | 5/2007 | Schmeling |
| 7,226,442 B2 | 6/2007 | Sheppard |
| 7,235,044 B2 | 6/2007 | Forsell |
| 7,239,918 B2 | 7/2007 | Strother |
| 7,242,980 B2 | 7/2007 | Eckerdal |
| 7,242,982 B2 | 7/2007 | Singhal |
| 7,248,926 B2 | 7/2007 | Woods |
| 7,248,929 B2 | 7/2007 | Meadows |
| 7,254,449 B2 | 8/2007 | Karunasiri |
| 7,260,435 B2 | 8/2007 | Ibrahim |
| 7,263,401 B2 | 8/2007 | Scott |
| 7,273,457 B2 | 9/2007 | Penner |
| 7,283,867 B2 | 10/2007 | Strother |
| 7,283,874 B2 | 10/2007 | Penner |
| 7,286,880 B2 | 10/2007 | Olson |
| 7,286,881 B2 | 10/2007 | Schommer |
| 7,295,878 B1 | 11/2007 | Meadows |
| 7,308,316 B2 | 12/2007 | Schommer |
| 7,313,441 B2 | 12/2007 | Mass |
| 7,317,947 B2 | 1/2008 | Wahlstrand |
| 7,319,901 B2 * | 1/2008 | Dublin et al. .................. 607/36 |
| 7,330,762 B2 | 2/2008 | Boveja |
| 7,337,010 B2 | 2/2008 | Howard |
| 7,349,741 B2 | 3/2008 | Maltan |
| 7,367,938 B2 | 5/2008 | Forsell |
| 7,369,897 B2 | 5/2008 | Boveja |
| 7,376,563 B2 | 5/2008 | Leysieffer |
| 7,379,775 B2 | 5/2008 | Parramon |
| 7,388,378 B2 | 6/2008 | Gray |
| 7,392,089 B2 | 6/2008 | Wahlstrand |
| 7,400,926 B2 | 7/2008 | Forsell |
| 7,426,445 B1 | 9/2008 | Fister |
| 7,428,438 B2 | 9/2008 | Parramon |
| 7,437,193 B2 | 10/2008 | Parramon |
| 7,437,644 B2 | 10/2008 | Ginggen |
| 7,444,184 B2 | 10/2008 | Boveja |
| 7,450,987 B2 | 11/2008 | Varrichio |
| 7,460,911 B2 | 12/2008 | Cosendai |
| 7,471,986 B2 | 12/2008 | Hatlestad |
| 7,482,783 B2 | 1/2009 | Schommer |
| 7,486,048 B2 | 2/2009 | Tsukamoto |
| 7,496,404 B2 | 2/2009 | Meadows |
| 7,499,753 B2 | 3/2009 | Forsell |
| 7,505,816 B2 | 3/2009 | Schmeling |
| 7,512,443 B2 | 3/2009 | Phillips |
| 7,513,257 B2 | 4/2009 | Schulman |
| 7,515,967 B2 | 4/2009 | Phillips |
| 7,529,586 B2 | 5/2009 | Wahlstrand |
| 7,529,589 B2 | 5/2009 | Williams |
| 7,532,933 B2 | 5/2009 | Hastings |
| 7,555,345 B2 | 6/2009 | Wahlstrand |
| 7,555,346 B1 | 6/2009 | Woods |
| 7,571,007 B2 | 8/2009 | Erickson |
| 7,582,387 B2 | 9/2009 | Howard |
| 7,587,241 B2 | 9/2009 | Parramon |
| 7,592,776 B2 | 9/2009 | Tsukamoto |
| 7,596,408 B2 | 9/2009 | Singhal |
| 7,599,743 B2 | 10/2009 | Hassler |
| 7,599,744 B2 | 10/2009 | Giordano |
| 7,617,001 B2 | 11/2009 | Penner |
| 7,621,863 B2 | 11/2009 | Forsell |
| 7,621,878 B2 | 11/2009 | Ericson |
| 7,623,827 B2 | 11/2009 | Ibrahim |
| 7,635,541 B2 | 12/2009 | Scott |
| 7,640,061 B2 | 12/2009 | He |
| 7,641,619 B2 | 1/2010 | Penner |
| 7,641,992 B2 | 1/2010 | Howard |
| 7,642,013 B2 | 1/2010 | Howard |
| 7,647,109 B2 | 1/2010 | Hastings |
| 7,648,455 B2 | 1/2010 | Forsell |
| 7,650,192 B2 | 1/2010 | Wahlstrand |
| 7,662,509 B2 | 2/2010 | Howard |
| 7,666,132 B2 | 2/2010 | Forsell |
| 7,670,363 B2 | 3/2010 | Vogel |
| 7,671,594 B2 | 3/2010 | Gray |
| 7,672,732 B2 | 3/2010 | Sun |
| 7,682,745 B2 | 3/2010 | Howard |
| 7,684,867 B2 | 3/2010 | Jaax |
| 7,711,433 B2 | 5/2010 | Davis |
| 7,711,435 B2 | 5/2010 | Schommer |
| 7,720,546 B2 | 5/2010 | Ginggen |
| 7,727,277 B2 | 6/2010 | Aharoni |
| 7,729,758 B2 | 6/2010 | Haller |
| 7,729,777 B2 | 6/2010 | Gray |
| 7,734,343 B2 | 6/2010 | Ransbury |
| 7,734,353 B2 | 6/2010 | Gerber |
| 7,736,390 B2 | 6/2010 | Aharoni |
| 7,738,965 B2 | 6/2010 | Phillips |
| 7,751,879 B2 | 7/2010 | Varrichio |
| 7,751,899 B1 | 7/2010 | Karunasiri |
| 7,751,902 B1 | 7/2010 | Karunasiri |
| 7,756,587 B2 | 7/2010 | Penner |
| 7,765,003 B2 | 7/2010 | Peters |
| 7,769,462 B2 | 8/2010 | Meadows |
| 7,774,066 B2 | 8/2010 | Deininger |
| 7,774,069 B2 | 8/2010 | Olson |
| 7,776,087 B2 | 8/2010 | Aharoni |
| 7,780,613 B2 | 8/2010 | Sherman |
| 7,782,190 B1 | 8/2010 | Martin |
| 7,792,588 B2 | 9/2010 | Harding |
| 7,794,869 B2 | 9/2010 | Howard |
| 7,801,613 B2 | 9/2010 | Li |
| 7,801,615 B2 | 9/2010 | Meadows |
| 7,803,481 B2 | 9/2010 | Howard |
| 7,805,200 B2 | 9/2010 | Kast |
| 7,807,299 B2 | 10/2010 | Howard |
| 7,811,705 B2 | 10/2010 | Scott |
| 7,813,809 B2 | 10/2010 | Strother |
| 7,818,068 B2 | 10/2010 | Meadows |
| 7,822,480 B2 | 10/2010 | Park |
| 7,839,146 B2 | 11/2010 | Gray |
| 7,848,814 B2 | 12/2010 | Torgerson |

(56) References Cited

U.S. PATENT DOCUMENTS

| | | |
|---|---|---|
| 7,848,817 B2 | 12/2010 | Janzig |
| 7,856,986 B2 | 12/2010 | Darley |
| 7,858,236 B2 | 12/2010 | Howard |
| 7,865,245 B2 | 1/2011 | Torgerson |
| 7,875,389 B2 | 1/2011 | Scott |
| 7,881,796 B2 | 2/2011 | Scott |
| 7,883,790 B2 | 2/2011 | Howard |
| 7,894,913 B2 | 2/2011 | Boggs |
| 7,899,554 B2 | 3/2011 | Williams |
| 7,904,167 B2 | 3/2011 | Klosterman |
| 7,904,170 B2 | 3/2011 | Harding |
| 7,917,213 B2 | 3/2011 | Bulkes |
| 7,925,357 B2 | 4/2011 | Phillips |
| 7,927,742 B2 | 4/2011 | Scott |
| 7,930,030 B2 | 4/2011 | Woods |
| 7,930,031 B2 | 4/2011 | Penner |
| 7,932,696 B2 | 4/2011 | Peterson |
| RE42,378 E | 5/2011 | Wolinsky |
| 7,945,334 B2 | 5/2011 | Jimenez |
| 7,949,393 B2 | 5/2011 | Varrichio |
| 7,952,349 B2 | 5/2011 | Huang |
| 7,962,211 B2 | 6/2011 | Torgerson |
| 7,979,126 B2 | 7/2011 | Payne |
| 7,988,616 B2 | 8/2011 | Forsell |
| 7,991,355 B2 | 8/2011 | Ibrahim |
| 8,005,547 B2 | 8/2011 | Forsberg |
| 8,010,205 B2 | 8/2011 | Rahman |
| 8,010,206 B2 | 8/2011 | Dai |
| RE42,682 E | 9/2011 | Barreras |
| 8,024,047 B2 | 9/2011 | Olson |
| 8,032,227 B2 | 10/2011 | Parramon |
| 8,036,736 B2 | 10/2011 | Snyder |
| 8,044,635 B2 | 10/2011 | Peterson |
| 8,060,214 B2 | 11/2011 | Larson |
| 8,086,313 B2 | 12/2011 | Singhal |
| 8,092,412 B2 | 1/2012 | Sherman |
| 8,095,221 B2 | 1/2012 | Varrichio |
| 8,096,938 B2 | 1/2012 | Forsell |
| 8,096,939 B2 | 1/2012 | Forsell |
| 8,099,169 B1 | 1/2012 | Karunasiri |
| 8,103,353 B1 | 1/2012 | Karunasiri |
| 8,105,714 B2 | 1/2012 | Schmidt |
| 8,112,157 B2 | 2/2012 | Tai |
| 8,115,448 B2 | 2/2012 | John |
| 8,116,883 B2 | 2/2012 | Williams |
| 8,126,558 B2 | 2/2012 | Forsell |
| 8,126,563 B2 | 2/2012 | Ibrahim |
| 8,140,168 B2 | 3/2012 | Olson |
| 8,147,543 B2 | 4/2012 | Forsell |
| 8,150,529 B2 | 4/2012 | Snell |
| 8,155,746 B2 | 4/2012 | Maltan |
| 8,155,752 B2 | 4/2012 | Aghassian |
| 8,162,924 B2 | 4/2012 | Boyden |
| 8,165,663 B2 | 4/2012 | Hyde |
| 8,165,678 B2 | 4/2012 | Forsberg |
| 8,165,692 B2 | 4/2012 | Strother |
| 8,165,694 B2 | 4/2012 | Carbanaru |
| 8,170,681 B2 | 5/2012 | Jimenez |
| 8,175,716 B2 | 5/2012 | Rahman |
| 8,175,717 B2 | 5/2012 | Haller |
| 8,180,452 B2 | 5/2012 | Shaquer |
| 8,185,212 B2 | 5/2012 | Carbunaru |
| 8,187,213 B2 | 5/2012 | Sherman |
| 8,193,766 B2 | 6/2012 | Rondoni |
| 8,195,304 B2 | 6/2012 | Strother |
| 8,204,602 B2 | 6/2012 | Kallmyer |
| 8,204,605 B2 | 6/2012 | Hastings |
| 8,214,042 B2 | 7/2012 | Ozawa |
| 2002/0065539 A1* | 5/2002 | Von Arx et al. ............ 607/60 |
| 2003/0135246 A1* | 7/2003 | Mass et al. ............ 607/60 |
| 2003/0171792 A1 | 9/2003 | Zarinetchi |
| 2004/0172102 A1 | 9/2004 | Leysieffer |
| 2004/0173221 A1 | 9/2004 | Singhal |
| 2004/0176815 A1 | 9/2004 | Janzig |
| 2004/0176818 A1 | 9/2004 | Wahlstrand |
| 2005/0075693 A1 | 4/2005 | Toy |
| 2005/0104577 A1 | 5/2005 | Matei |
| 2005/0113887 A1 | 5/2005 | Bauhahn |
| 2005/0119716 A1 | 6/2005 | McClure |
| 2005/0288739 A1 | 12/2005 | Hassler |
| 2006/0020306 A1 | 1/2006 | Davis |
| 2006/0183965 A1 | 8/2006 | Kasic |
| 2007/0015959 A1 | 1/2007 | Forsell |
| 2007/0060968 A1 | 3/2007 | Strother |
| 2007/0060980 A1 | 3/2007 | Strother |
| 2007/0066995 A1 | 3/2007 | Strother |
| 2007/0073099 A1 | 3/2007 | Forsell |
| 2007/0142728 A1 | 6/2007 | Penner |
| 2007/0150037 A1 | 6/2007 | Hastings |
| 2007/0150038 A1 | 6/2007 | Hastings |
| 2007/0208390 A1 | 9/2007 | Von Arx |
| 2007/0232848 A1 | 10/2007 | Forsell |
| 2007/0233019 A1 | 10/2007 | Forsell |
| 2007/0239224 A1 | 10/2007 | Bennett |
| 2007/0270921 A1 | 11/2007 | Strother |
| 2007/0279020 A1 | 12/2007 | Mozzi |
| 2007/0293914 A1 | 12/2007 | Woods |
| 2008/0020278 A1 | 1/2008 | Schmidt |
| 2008/0021505 A1 | 1/2008 | Hastings |
| 2008/0027500 A1 | 1/2008 | Chen |
| 2008/0033500 A1 | 2/2008 | Strother |
| 2008/0044728 A1 | 2/2008 | Schmidt |
| 2008/0051854 A1 | 2/2008 | Bulkes |
| 2008/0082143 A1 | 4/2008 | Dai |
| 2008/0092911 A1 | 4/2008 | Schulman |
| 2008/0103543 A1 | 5/2008 | Li |
| 2008/0103556 A1 | 5/2008 | Li |
| 2008/0109054 A1 | 5/2008 | Hastings |
| 2008/0161874 A1 | 7/2008 | Bennett |
| 2008/0177353 A1 | 7/2008 | Hirota |
| 2008/0221555 A1 | 9/2008 | Sheppard |
| 2008/0275296 A1 | 11/2008 | Forsell |
| 2008/0294207 A1 | 11/2008 | Kast |
| 2008/0300660 A1 | 12/2008 | John |
| 2008/0319512 A1 | 12/2008 | Sherman |
| 2009/0018599 A1 | 1/2009 | Hastings |
| 2009/0024179 A1 | 1/2009 | Dronov |
| 2009/0048524 A1 | 2/2009 | Wildau |
| 2009/0048643 A1 | 2/2009 | Erickson |
| 2009/0054725 A1 | 2/2009 | Forsell |
| 2009/0069869 A1 | 3/2009 | Stouffer |
| 2009/0093713 A1 | 4/2009 | Hyde |
| 2009/0093728 A1 | 4/2009 | Hyde |
| 2009/0112291 A1 | 4/2009 | Wahlstrand |
| 2009/0118796 A1 | 5/2009 | Chen |
| 2009/0157147 A1 | 6/2009 | Cauller |
| 2009/0157148 A1 | 6/2009 | Phillips |
| 2009/0163964 A1 | 6/2009 | Boyden |
| 2009/0163965 A1 | 6/2009 | Boyden |
| 2009/0163977 A1 | 6/2009 | Boyden |
| 2009/0177139 A1 | 7/2009 | Boyden |
| 2009/0177254 A1 | 7/2009 | Boyden |
| 2009/0182388 A1 | 7/2009 | Von Arx |
| 2009/0198293 A1 | 8/2009 | Cauller |
| 2009/0204170 A1 | 8/2009 | Hastings |
| 2009/0216296 A1 | 8/2009 | Meskens |
| 2009/0222066 A1 | 9/2009 | Chen |
| 2009/0228077 A1 | 9/2009 | Ginggen |
| 2009/0228078 A1 | 9/2009 | Zhang |
| 2009/0234420 A1 | 9/2009 | Wahlstrand |
| 2009/0240100 A1 | 9/2009 | Forsell |
| 2009/0240294 A1 | 9/2009 | Forsell |
| 2009/0240303 A1 | 9/2009 | Wahlstrand |
| 2009/0247817 A1 | 10/2009 | Forsell |
| 2009/0247818 A1 | 10/2009 | Forsell |
| 2009/0248109 A1 | 10/2009 | Forsell |
| 2009/0250068 A1 | 10/2009 | Forsell |
| 2009/0254106 A1 | 10/2009 | Forsell |
| 2009/0259273 A1 | 10/2009 | Figueiredo |
| 2009/0270951 A1* | 10/2009 | Kallmyer ............ 607/61 |
| 2009/0274849 A1 | 11/2009 | Scott |
| 2009/0276014 A1 | 11/2009 | Morgan |
| 2009/0276015 A1 | 11/2009 | Rondoni |

(56) References Cited

U.S. PATENT DOCUMENTS

| | | |
|---|---|---|
| 2009/0276016 A1 | 11/2009 | Phillips |
| 2009/0292336 A1 | 11/2009 | Nishida |
| 2010/0003656 A1 | 1/2010 | Kilgard |
| 2010/0004705 A1 | 1/2010 | Kilgard |
| 2010/0004717 A1 | 1/2010 | Kilgard |
| 2010/0007307 A1 | 1/2010 | Baarman |
| 2010/0010582 A1 | 1/2010 | Carbunaru |
| 2010/0049277 A1 | 2/2010 | Wahlstrand |
| 2010/0063347 A1 | 3/2010 | Yomtov |
| 2010/0106028 A1 | 4/2010 | Penner |
| 2010/0106223 A1 | 4/2010 | Grevious |
| 2010/0114253 A1 | 5/2010 | Wahlstrand |
| 2010/0137948 A1 | 6/2010 | Aghassian |
| 2010/0145139 A1 | 6/2010 | Forsell |
| 2010/0145412 A1 | 6/2010 | Boyden |
| 2010/0174346 A1 | 7/2010 | Boyden |
| 2010/0204756 A1 | 8/2010 | Aghassian |
| 2010/0210955 A1 | 8/2010 | Forsell |
| 2010/0211091 A1 | 8/2010 | Forsell |
| 2010/0211092 A1 | 8/2010 | Forsell |
| 2010/0211133 A1 | 8/2010 | Forsell |
| 2010/0211134 A1 | 8/2010 | Forsell |
| 2010/0217067 A1 | 8/2010 | Forsell |
| 2010/0217295 A1 | 8/2010 | Forsell |
| 2010/0217352 A1 | 8/2010 | Forsell |
| 2010/0217353 A1 | 8/2010 | Forsell |
| 2010/0222847 A1 | 9/2010 | Goetz |
| 2010/0222848 A1 | 9/2010 | Forsell |
| 2010/0222849 A1 | 9/2010 | Forsell |
| 2010/0228079 A1 | 9/2010 | Forsell |
| 2010/0234792 A1 | 9/2010 | Dacey |
| 2010/0234793 A1 | 9/2010 | Dacey |
| 2010/0234922 A1 | 9/2010 | Forsell |
| 2010/0240017 A1 | 9/2010 | Dacey |
| 2010/0241048 A1 | 9/2010 | Dacey |
| 2010/0241049 A1 | 9/2010 | Dacey |
| 2010/0241050 A1 | 9/2010 | Dacey |
| 2010/0241051 A1 | 9/2010 | Dacey |
| 2010/0241052 A1 | 9/2010 | Dacey |
| 2010/0241053 A1 | 9/2010 | Dacey |
| 2010/0241054 A1 | 9/2010 | Dacey |
| 2010/0241055 A1 | 9/2010 | Dacey |
| 2010/0241194 A1 | 9/2010 | Kast |
| 2010/0249692 A1 | 9/2010 | Dacey |
| 2010/0249886 A1 | 9/2010 | Park |
| 2010/0249888 A1 | 9/2010 | Glenn |
| 2010/0256709 A1 | 10/2010 | Kallmyer |
| 2010/0256710 A1 * | 10/2010 | Dinsmoor et al. ............... 607/61 |
| 2010/0274310 A1 | 10/2010 | Boggs |
| 2010/0292629 A1 | 11/2010 | Dacey |
| 2010/0305662 A1 | 12/2010 | Ozawa |
| 2010/0305663 A1 | 12/2010 | Aghassian |
| 2010/0312310 A1 | 12/2010 | Meskens |
| 2010/0316898 A1 | 12/2010 | Howard |
| 2010/0324354 A1 | 12/2010 | Peters |
| 2010/0331917 A1 | 12/2010 | Digiore |
| 2010/0331918 A1 | 12/2010 | Digiore |
| 2010/0331919 A1 | 12/2010 | Digiore |
| 2010/0331920 A1 | 12/2010 | Digiore |
| 2011/0004269 A1 | 1/2011 | Strother |
| 2011/0004278 A1 | 1/2011 | Aghassian |
| 2011/0009924 A1 | 1/2011 | Meskens |
| 2011/0015473 A1 | 1/2011 | Forsell |
| 2011/0015474 A1 | 1/2011 | Forsell |
| 2011/0022125 A1 | 1/2011 | Olson |
| 2011/0040143 A1 | 2/2011 | Forsell |
| 2011/0046699 A1 | 2/2011 | Mazanec |
| 2011/0046730 A1 | 2/2011 | Meskens |
| 2011/0054563 A1 | 3/2011 | Janzig |
| 2011/0060386 A1 | 3/2011 | Woods |
| 2011/0066254 A1 | 3/2011 | Forsell |
| 2011/0071597 A1 | 3/2011 | Aghassian |
| 2011/0077720 A1 | 3/2011 | Torgerson |
| 2011/0087307 A1 | 4/2011 | Carbunaru |
| 2011/0087337 A1 | 4/2011 | Forsell |
| 2011/0093048 A1 | 4/2011 | Aghassian |
| 2011/0106219 A1 | 5/2011 | Cauller |
| 2011/0112610 A1 | 5/2011 | Rahman |
| 2011/0112612 A1 | 5/2011 | Rahman |
| 2011/0133699 A1 | 6/2011 | Howard |
| 2011/0137378 A1 | 6/2011 | Klosterman |
| 2011/0144468 A1 | 6/2011 | Boggs |
| 2011/0144566 A1 | 6/2011 | Dacey |
| 2011/0152750 A1 | 6/2011 | Dacey |
| 2011/0152751 A1 | 6/2011 | Dacey |
| 2011/0152752 A1 | 6/2011 | Dacey |
| 2011/0152789 A1 | 6/2011 | Dacey |
| 2011/0152790 A1 | 6/2011 | Dacey |
| 2011/0152978 A1 | 6/2011 | Dacey |
| 2011/0160643 A1 | 6/2011 | Dacey |
| 2011/0160644 A1 | 6/2011 | Dacey |
| 2011/0160681 A1 | 6/2011 | Dacey |
| 2011/0160804 A1 | 6/2011 | Penner |
| 2011/0166630 A1 | 7/2011 | Phillips |
| 2011/0175568 A1 | 7/2011 | Leijssen |
| 2011/0178576 A1 | 7/2011 | Aghassian |
| 2011/0184230 A1 | 7/2011 | Forsell |
| 2011/0190853 A1 | 8/2011 | Dinsmoor |
| 2011/0192402 A1 | 8/2011 | Forsell |
| 2011/0196452 A1 | 8/2011 | Forsell |
| 2011/0208021 A1 | 8/2011 | Goodall |
| 2011/0208023 A1 | 8/2011 | Goodall |
| 2011/0208026 A1 | 8/2011 | Goodall |
| 2011/0208231 A1 | 8/2011 | Forsell |
| 2011/0218382 A1 | 9/2011 | Orejola |
| 2011/0230930 A1 | 9/2011 | Forsell |
| 2011/0230935 A1 | 9/2011 | Zdeblick |
| 2011/0234155 A1 | 9/2011 | Chen |
| 2011/0273138 A1 | 11/2011 | Baarman |
| 2011/0275912 A1 | 11/2011 | Boyden |
| 2011/0276110 A1 | 11/2011 | Whitehurst |
| 2011/0276111 A1 | 11/2011 | Carbunaru |
| 2011/0280426 A1 | 11/2011 | Bachler |
| 2011/0281148 A1 | 11/2011 | Scott |
| 2011/0282134 A1 | 11/2011 | Forsell |
| 2011/0287717 A1 | 11/2011 | Ibrahim |
| 2011/0288499 A1 | 11/2011 | Forsell |
| 2011/0288615 A1 | 11/2011 | Armstrong |
| 2011/0295088 A1 | 12/2011 | Boyden |
| 2011/0295089 A1 | 12/2011 | Boyden |
| 2011/0295090 A1 | 12/2011 | Boyden |
| 2011/0295159 A1 | 12/2011 | Shachar |
| 2011/0301667 A1 | 12/2011 | Olson |
| 2011/0301669 A1 | 12/2011 | Olson |
| 2011/0313490 A1 | 12/2011 | Parramon |
| 2011/0319703 A1 | 12/2011 | Wiskerke |
| 2011/0319785 A1 | 12/2011 | Snyder |
| 2012/0004708 A1 | 1/2012 | Chen |
| 2012/0004709 A1 | 1/2012 | Chen |
| 2012/0007441 A1 | 1/2012 | John |
| 2012/0010481 A1 | 1/2012 | Goodall |
| 2012/0012630 A1 | 1/2012 | Lui |
| 2012/0019201 A1 | 1/2012 | Peterson |
| 2012/0035687 A1 | 2/2012 | Lu |
| 2012/0041285 A1 | 2/2012 | Goodall |
| 2012/0041286 A1 | 2/2012 | Goodall |
| 2012/0041287 A1 | 2/2012 | Goodall |
| 2012/0041515 A1 | 2/2012 | Meskens |
| 2012/0046712 A1 | 2/2012 | Woods |
| 2012/0053657 A1 | 3/2012 | Parker |
| 2012/0059431 A1 | 3/2012 | Williams |
| 2012/0095528 A1 | 4/2012 | Miller |
| 2012/0101874 A1 | 4/2012 | Ben-Haim |
| 2012/0123505 A1 | 5/2012 | Kothandaraman |
| 2012/0130448 A1 | 5/2012 | Woods |
| 2012/0139485 A1 | 6/2012 | Olson |
| 2012/0150259 A1 | 6/2012 | Meskens |
| 2012/0172947 A1 | 7/2012 | Rahman |
| 2012/0172948 A1 | 7/2012 | Aghassian |

\* cited by examiner

RECHARGING AND COMMUNICATION LEAD FOR AN IMPLANTABLE DEVICE

BACKGROUND OF THE INVENTION

1. Field of the Invention

The present disclosure generally relates to communication and recharging elements that are used for implantable electrical devices. More particularly, the present disclosure relates to an implantable lead having multiple charging and/or communication elements.

2. Description of the Related Art

There are a variety of implantable devices for which it is desirable to provide remote communication and electrical recharging. Such devices can include pacemakers, implantable drug delivery systems and nerve stimulation devices. Among the latter are implantable devices for nerve stimulation, such as vagus nerve stimulation (VNS). VNS has been used as a treatment for intractable epilepsy. VNS is achieved through an implanted pulse generator that delivers a bipolar, biphasic pulse to the vagus nerve. The implant procedure is very similar to the implantation of a pacemaker. The generator is implanted subcutaneously, typically in the upper left chest wall. An electric lead is connected between the pulse generator and one or more electrodes on the vagus nerve using a subcutaneous tunneling tool to the left vagus nerve, which lies in the carotid sheath.

Many implantable devices were originally designed with non-rechargeable batteries. More recently, however, rechargeable devices have been developed, allowing a user to periodically recharge the device using an inductive charging device that is magnetically coupled between the inductive recharging elements of the implanted device and an external recharger device having corresponding inductive elements. However, such recharging presents several challenges. In typical implantable devices, the inductive recharging elements of the implanted device are located in the body of the device itself, such as the pulse generator unit of the VNS system described above. Unfortunately, the depth of implantation of the device affects charging time and power usage because the casing of the implanted device and soft tissue between the device and the recharger have the effect of attenuating power transfer. Additionally, recharging takes time—typically several hours. Positioning the recharger in a specific orientation on the individual for an extended period of time can be difficult. It is desirable that the recharging elements of the implanted device are properly aligned with the recharger—for example, directly over the implanted device. However, the positioning of the recharger in a fixed location for an extended period of time can be a challenge due to varying body profiles (which can also change with time) and any movement of the individual. Furthermore, recharging can cause heating of the implanted device, potentially damaging surrounding tissue.

Similar challenges relate to communications with such devices. With many implantable devices, it can be desirable to provide programming commands, such as from a programmer or patient monitoring device, to adjust the device's operation. These commands can be transmitted to an antenna of the device using the medical information communication system (MICS). However, soft and fatty tissue between the antenna and the transmitter increase the power required for these transmissions.

It is desirable to provide safe, simple, and convenient recharging and communications with implanted devices. It is believed that many current implantable devices fall short in this area. The present disclosure is directed to overcoming, or at least reducing the effects, of one or more of the issues set forth above.

SUMMARY OF THE INVENTION

It has been recognized that it would be advantageous to develop an electrical recharging system for an implantable medical device that provides rapid recharging and is less susceptible to variations in patient profile, movement and implantation depth.

It has also been recognized that it would be advantageous to develop a communications system for an implantable medical device that easily places the communications antenna in a desirable position for communication transfer.

In accordance with one aspect thereof, the present disclosure provides a lead for an implantable medical device (IMD) that includes a flexible, implantable tether, electrically connectable to the IMD, and two or more control elements, disposed along the tether. The control elements are electrically interconnectable to the IMD, and configured to transmit power and/or communication signals thereto.

In accordance with another aspect thereof, the present disclosure provides a system suitable for implantation into a human or animal body. The system includes a programmable device, having a rechargeable battery, and a flexible tether, electrically connected to the programmable device. The tether includes two or more integrated control elements, disposed along a length thereof, the control elements being configured to transmit power and/or control signals to the programmable device.

In accordance with yet another aspect thereof, the disclosure provides a vagus nerve stimulation system, including an implantable programmable pulse generation device, having a rechargeable battery, an implantable electrode, attachable to the vagus nerve, and an implantable flexible tether. The tether electrically interconnects the pulse generation device and the electrode, and includes two or more integrated control elements disposed along a length thereof.

These and other embodiments of the present application will be discussed more fully in the description. The features, functions, and advantages can be achieved independently in various embodiments of the claimed invention, or may be combined in yet other embodiments.

Figure 1:
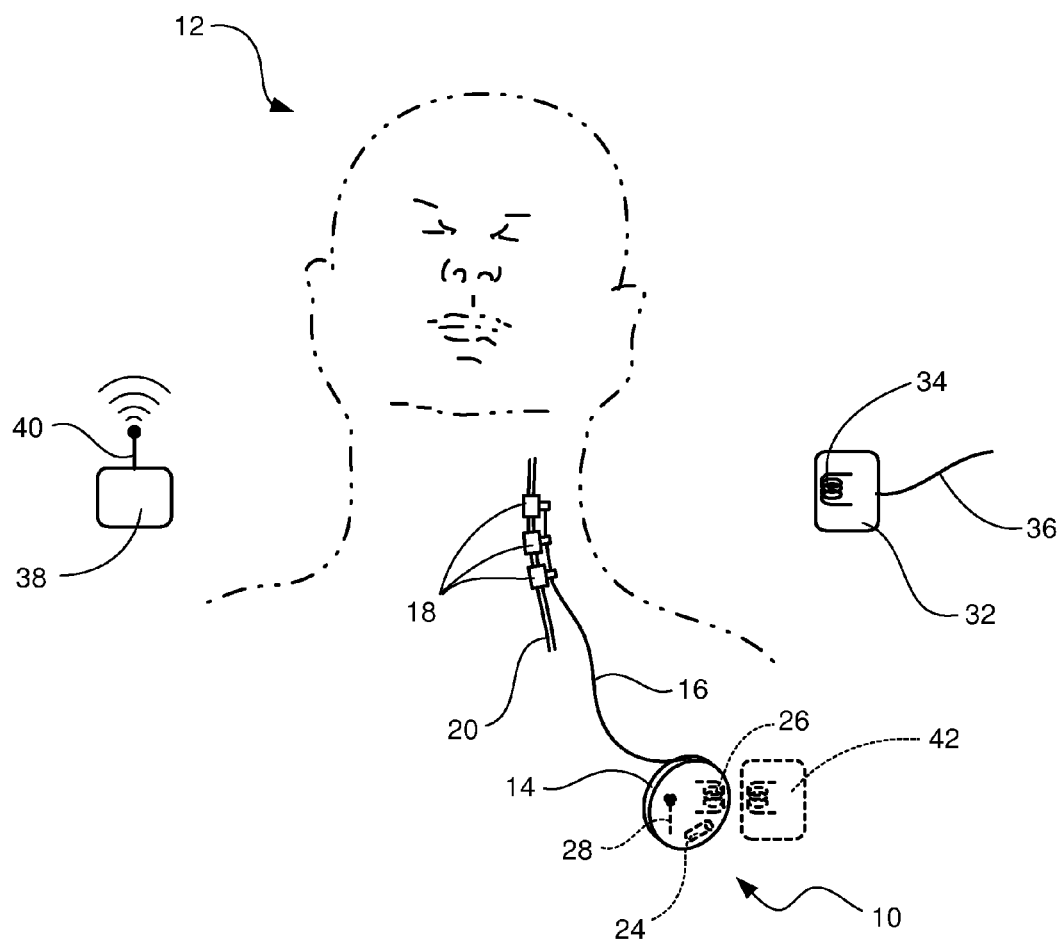
FIG. 1 is a schematic representation of a human subject showing a subcutaneous vagus nerve stimulation system, having a lead extending from a pulse generator device to electrodes attached at the left vagus nerve.

While the disclosure is susceptible to various modifications and alternative forms, specific embodiments have been shown by way of example in the drawings and will be described in detail herein. However, it should be understood that the disclosure is not intended to be limited to the particular forms disclosed. Rather, the intention is to cover all modifications, equivalents and alternatives falling within the spirit and scope as defined by the appended claims.

DESCRIPTION OF ILLUSTRATIVE EMBODIMENTS

Illustrative embodiments are described below as they might be employed in a lead for an implantable device, and a system employing the same. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

Further aspects and advantages of the various embodiments will become apparent from consideration of the following description and drawings. These embodiments are described in sufficient detail to enable those skilled in the art to practice the invention, and it is to be understood that modifications to the various disclosed embodiments may be made, and other embodiments may be utilized, without departing from the spirit and scope of the present invention. The following detailed description is, therefore, not to be taken in a limiting sense.

As used herein, the term "implantable" means a device that can be completely subcutaneously implanted into a human or animal body, with no portions of the apparatus extending outside the body after implantation.

As used herein, the term "implantable device" means any type of electrical device that is implantable into a human or animal body, and is configured to affect the function of the body. A device that affects the function of the body can also be called an active implantable medical device or simply an implantable medical device (IMD). Examples of implantable medical devices include cardiac pacemakers, nerve stimulation devices, and implantable drug delivery devices.

As noted above, there are a variety of implantable devices for which it is desirable to provide remote communication and electrical recharging. Such devices include implantable devices for nerve stimulation, such as VNS. VNS was approved by the FDA in 1998 as an adjunctive therapy for epilepsy with partial onset seizures. Shown in FIG. 1 is a schematic diagram of one embodiment of an implantable vagus nerve stimulation system, indicated generally at 10, implanted into a patient 12. The system includes two main components: a pulse generator 14, and a tether or lead 16 that has one or more electrodes 18 at its distal end. The tether and electrodes are collectively referred to as the lead, and the lead provides an interface between the pulse generator 14 and the electrodes 18. The electrodes 18 are attachable to the vagus nerve 20. An implantable VNS system of this type is known to those of skill in the art, and is commercially available, such as from Cyberonics, Inc. of Houston, Tex.

The pulse generator 14 can be a multi-programmable device, which allows a physician to control several parameters. In one embodiment, the programmable parameters are signal amplitude (e.g. 0-3.5 mA), frequency (e.g. 1-30 Hz), pulse width (e.g. 130-1000 μs), signal ON time (e.g. 7-60 sec) and signal OFF time (e.g. 0.2-180 min). It is to be appreciated that these pulse parameters are only exemplary, and that other parameters and ranges can be used. The pulses can be delivered at the specified amplitude and frequency over the course of the ON time, and then during the OFF time, no stimulation takes place. This type of device typically does not stimulate continuously because it has been found that the antiepileptic effect tends to last much longer than the actual time of stimulation. In one embodiment, pulse settings can be 2 mA, at 25 Hz frequency, 250 μs is pulse width, with a 30 sec ON time, and 5 min OFF time. The variability in parameters allows for the physician to adjust for greater efficacy or less severe side effects, depending on the patient.

The implantable VNS system 10 includes additional elements for recharging and communication. As shown in FIG. 1, the pulse generation device 14 includes a rechargeable battery 24, a recharging induction coil 26, and an antenna 28. The battery and recharging coil operate in conjunction with a recharging device 32, which also includes an induction coil 34 and a connection 36 to a source of electrical power (not shown). In order to recharge the battery 24 of the pulse generation device 14, the recharging device 32 is placed in a location so that the coil 34 of the recharging device 32 is as near as possible to the coil 26 of the pulse generation device 14, so that the two coils become electro-magnetically linked through inductive coupling. The recharging device 32 can include an indicator light or other device (not shown) that gives feedback to indicate when the electro-magnetic charging link has been made. When an alternating electric current is supplied to the coil 34 of the recharging device 32, the electric field that is created induces an electrical current in the coil 26 of the pulse generation device 14, without any mechanical connection or direct contact between the two devices. The two coils become electro-magnetically linked through inductive coupling, allowing power to flow from one to the other. In this way, the recharging device 32, which is outside the body, can recharge the battery 24 of the pulse generation device 14, which is inside the body. Many rechargeable, implantable devices operate this way.

The antenna 28 of the pulse generation device 14 is configured to receive programming and control instructions from a communications device 38 that also has an antenna 40. Programming and control instructions can be transmitted to circuitry (not shown) of the pulse generation device 14 from the communications device 38, and these are received by the antenna 28. Likewise, data regarding operation of the pulse generation device 14 can also be transmitted to the communications device 38 in a similar manner. Communications and control with implanted devices is well known and widely used. Devices such as pacemakers and the like are routinely programmed and/or controlled via wireless communication using the Medical Information Communication System (MICS), which uses radio waves transmit information to and from implanted devices.

As noted above, in many rechargeable implantable devices, the inductive recharging and communication elements of the implanted device are located in the body of the device itself, such as the pulse generator unit of the VNS system 10 shown in FIG. 1. Unfortunately, the depth of implantation of the device affects communications transfer, as well as charging time and power usage because the casing of the implanted device (e.g., titanium) and soft tissue between the device and the recharger can have the effect of attenuating both radio waves and power transfer between induction coils. It is desirable that the recharging coil 26 of the implanted device 14 be properly aligned with the coil 34 of the recharger 32—for example, directly over the implanted device 14, as shown in dashed lines at 42. However, positioning a recharger 32 in a specific orientation on an individual for an extended period of time can be difficult. Rechargeable batteries can take 2-3 hours to recharge, and movement of the patient 12, as well as variations in a patient's anatomy, can contribute to moving the recharger 32 out of a desired position. This can cause recharging to take longer. This problem is particularly noticed with children and patients with special needs. While harnesses, belts, and other devices can be used to hold the recharger 32 in place, these devices are restrictive, and are not tolerated well by the patients who need them the most. Furthermore, poor placement during recharging can cause the implanted device and/or coils to heat more than normal, which may damage surrounding tissue.

Advantageously, the inventors have developed a system for recharging and communications with implanted devices that is safe, simple and robust. A perspective view of a human subject 50 having an implanted vagus nerve stimulation system 52 with a lead 54 having multiple integrated charging and communications elements 56 is provided in FIG. 2. To allow for movement of the patient and movement of the implanted elements within the patient's anatomy, the lead 54 can trace an irregular or undulating path, such as including small loops 58 for strain relief. The lead interconnects the pulse generation device 60 with a group of electrodes 62, which are placed along the vagus nerve 64.

Figure 2:
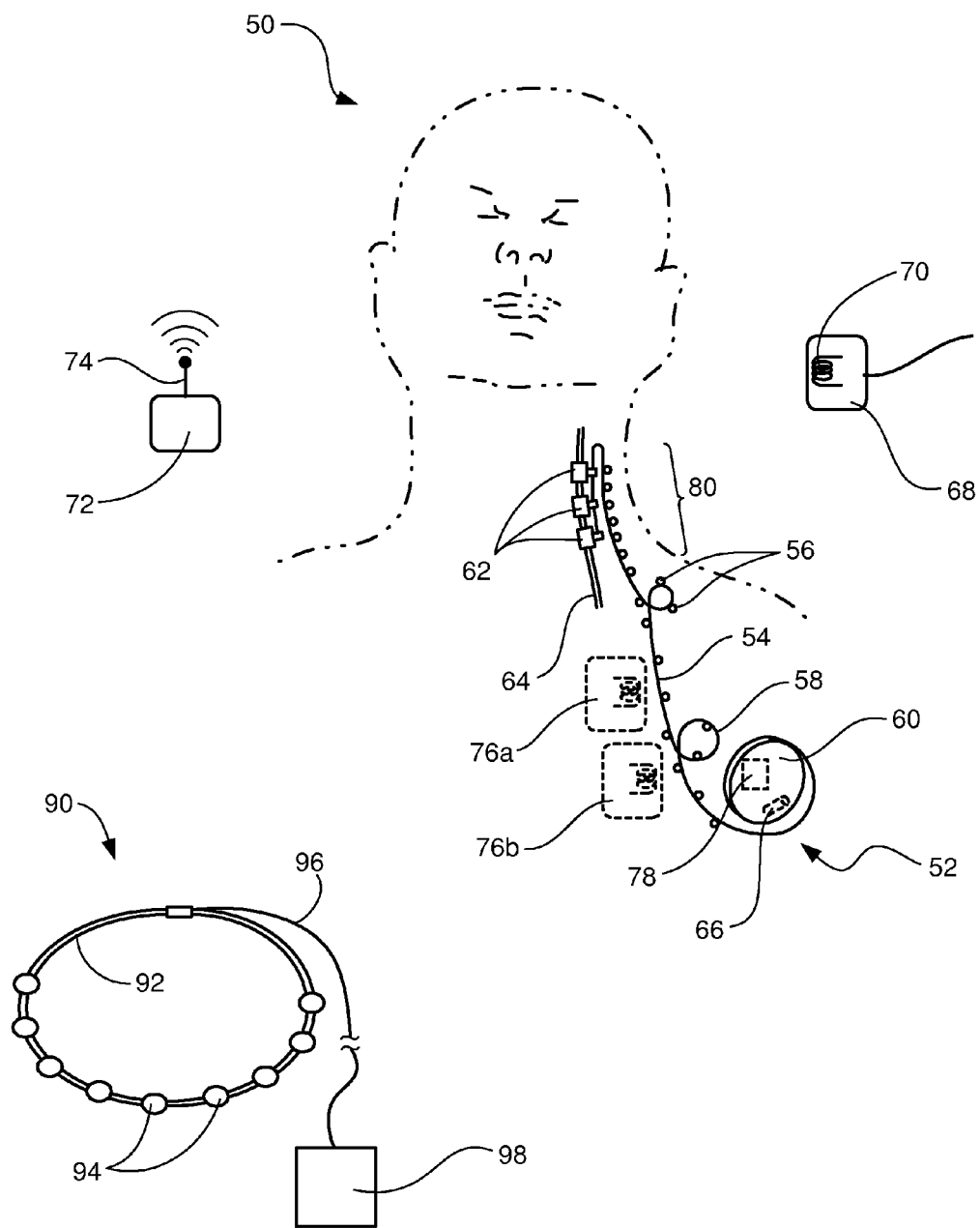
FIG. 2 is a schematic representation of a human subject showing a subcutaneous vagus nerve stimulation system, having a lead extending from a pulse generator device to electrodes attached at the left vagus nerve, the lead including multiple integrated charging and communications elements.

Like the embodiment shown in FIG. 1, the embodiment of FIG. 2 includes a rechargeable battery 66, associated with the pulse generation device 60. A recharging device 68 having an induction coil 70 is provided for use in recharging the battery through inductive coupling, as described above. Likewise, a communicating ancillary device 72 (e.g. a programmer, patient monitoring device, etc.) having an antenna 74 is also provided for communication with the pulse generation device 60. Unlike the embodiment of FIG. 1, the pulse generation device or controller 60 does not include a recharging coil or an antenna inside the controller unit itself. Instead, a plurality of integrated charging and communications elements 56 are positioned along the lead 54.

The integrated charging and communications elements 56 can be referred to as control elements, and can include at least one of a recharging coil and an antenna. In one embodiment, a single coil may function as both the recharging coil and as an antenna or different elements may be used for each function. The external components (external recharger and signal transmitter) may also be combined within the same device. These control elements 56 can transmit communication signals to the controller, and/or transmit power to the controller. For communications, the charging and communications elements 56 can be configured to receive either short or long range communications signals. Communications with an implanted device is enhanced when the implanted communications antenna is at a shallow depth in the body. The shallower the depth of the communications element, the less power is needed to transmit and receive a signal through the soft tissue. By incorporating multiple communication antennas or equivalent elements into the lead, a surgeon implanting the lead has the flexibility to route the lead close to the skin. For a VNS system, if routing the lead near to the skin is not an option, the lead by design will place the communication elements near the skin in the neck region due the minimal amount of soft tissue in that region. With less fatty tissue between the implanted device and the communicating ancillary device 72, communication to and from the implanted device 60 will be more efficient. The external recharger may also receive feedback from the communication elements to provide information to the user about the quality of the inductive link and battery charge status.

With respect to recharging, instead of requiring the recharging device 68 to be carefully placed in a specific position with respect to the pulse generation device 60, the provision of multiple recharging elements 56 in the lead 54 allows the recharger 68 to be placed anywhere along the route of the lead 54. The lead 54 creates multiple suitable positions at which the recharging device 68 can be placed and still provide effective electro-magnetic coupling, exemplary positions being indicated in dashed lines at 76a, 76b, in FIG. 2. This allows more freedom of placement of the recharger 68 and more freedom of movement for the patient 50 during recharging. It is also believed that this configuration can provide shorter recharge times on average.

Figure 3:
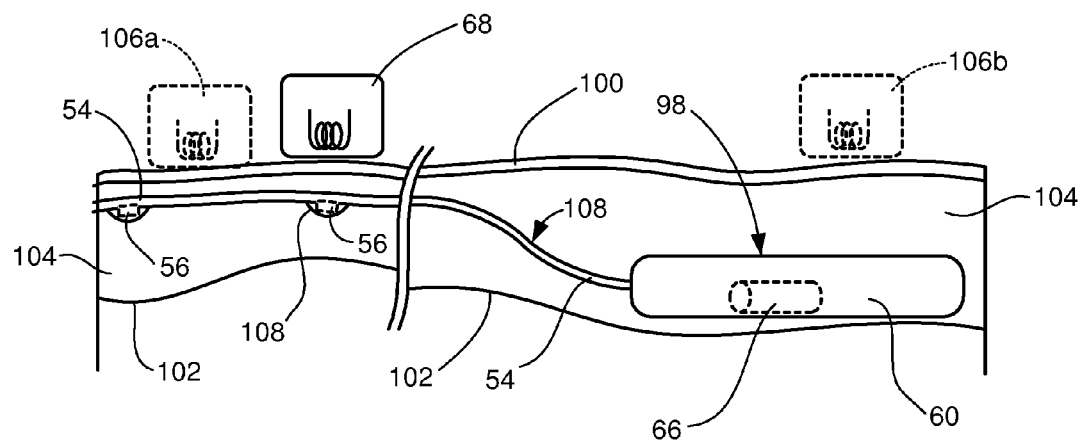
FIG. 3 is a partial cross-sectional view showing an embodiment of an implanted pulse generation device and a portion of a lead attached to the device, the lead having an integrated charging and communications element attached thereto.

This aspect of the implantable system is also illustrated in FIG. 3, which provides a partial cross-sectional view of a patient's anatomy, showing the implanted pulse generation device or controller 60 having a rechargeable battery 66, and a portion of the lead 54 attached to the device. The controller can have an outer case 98 of titanium, which is often used in medical applications because it is biologically inert and relatively resistant to degradation in the body. The lead 54 includes integrated charging and communications elements 56 attached thereto. In this view a common aspect of implantable devices is illustrated. The pulse generation device or controller 60 is implanted relatively deeply below the skin 100 and above deeper structures, such as underlying muscle 102, with a relatively large thickness of subcutaneous tissue 104 between the unit and the skin 100. Relatively deep implantation of the controller 60 is desirable for comfort of the patient and protection of the controller device itself. However, this relatively deep implantation can hinder recharging and communication, as discussed above.

The embodiment shown in FIGS. 2 and 3 helps deal with these issues. It can be seen from FIG. 3 that the lead 54 is implanted within the subcutaneous tissue 104, but relatively close to the skin 100. This places the multiple control elements 56 relatively close to the skin, and thereby closer to the recharging device 68 when it is placed near the outside surface of the skin. The provision of multiple control elements allows greater freedom of placement of the recharging device. For example, as shown at 106a, if the recharging device is not placed directly over any one recharging element 56, it will still be closer to the nearest recharging element than it would be if the recharging element were associated with the controller 60, and the recharging device were to be placed at a location like that shown at 106b. Placing the recharging elements closer to the skin also allows greater power transfer efficiency by reducing the distance between adjacent power transfer coils. Additionally, with multiple recharging elements in close proximity, an electromagnetic charge link can be established with multiple recharging elements at the same time, thus potentially leading to faster recharging. Where the recharging device 68 is not accurately aligned with any one recharging element 56, such as shown at 106a, but is in reasonable proximity with more than one such element, it can provide recharging energy to more than one element at a time.

An additional device that takes advantage of this freedom for recharging is also shown in FIG. 2. The implantable device system 52 can include a wearable recharging device 90 that can be configured as a necklace, for example, having a flexible, openable cord 92, with a plurality of recharging elements 94 disposed along its length. These recharging elements can be configured like the recharging device 68 shown in FIG. 2. The necklace-type recharging device 90 can include a power cord 96 that is attachable to a power source 98, whether AC or DC supplied by a circuit or a battery, with appropriate electronics to produce the desired voltage, current, etc. The necklace-type recharging device 90 can be worn around a patient's neck during a recharge time period, and since it has multiple recharging elements, at least one of the recharging elements is likely to be proximate to one or more of the recharging elements 56 of the lead 54. In this way, movement of the patient 50, movement of the recharging device 90, or movement of the lead 54 or controller 60 within the patient 50 can be tolerated to a greater degree without interfering with recharging of the device 60. This can also make finding a suitable charge location easier. It is to be understood that while a necklace-type recharging device is shown in FIG. 2, other configurations for the recharger can also be used. For example, a collar, vest, band or harness configuration can also be used, and these can be provided with single or multiple recharging elements.

As shown in FIG. 3, the lead 54 and each control element 56 can be encased within a continuous bio-compatible elastomeric casing 108 that protects the lead and the control elements from degradation. The lead can include different numbers of wires in different embodiments. Two wires in the lead can be used to carry stimulus pulses to the electrodes 62. Two additional wires can be used to carry power from charging elements 56 to the controller 60. Communication from each control element 56 to the controller 60 can also be provided by two additional wires. In this sort of configuration, the lead with multiple control elements in use with a nerve stimulation system like that shown in FIG. 2 can include six wires, with the communication and charging elements each being connected in series along a respective pair of wires. Since it does not matter which control elements receive the charging or communications signals, a single pair of wires can be used for each purpose.

Alternatively, the lead 54 can include two exclusive wires for each control element 56, with each unique pair of wires extending back to the controller 60 to provide charging and/or communications signals. It is to be understood that this configuration is likely to be more bulky than placing the control elements in series.

In another embodiment, the lead 54 includes a bus of wires shared by some or all of the control elements 56, which is connected to the controller 60. For example, each control element 56 can provide charging and/or communication signals to the controller 60 through wires bundled in the bus because the bus is connected and shared between all of the control elements 56. A single control element is selected, or multiplexed, via control logic and a control wire to omit cross-talk on the wires of the bus because the wires are shared between multiple control elements 56. The bus may contain numerous wires, for example: control element 56 logic control wire, a communication signal wire, a recharging power transmission wire, a data wire, a V+ wire supplying power to the control element 56 (e.g., Vdd, Vcc, HI, or power), or a V− wire supplying power to the control element 56 (e.g., Vee, Vss, LOW, or ground). Lead 54 can have one or more busses, and can have a bus dedicated to recharging and another bus dedicated to communication signals.

Figure 4:
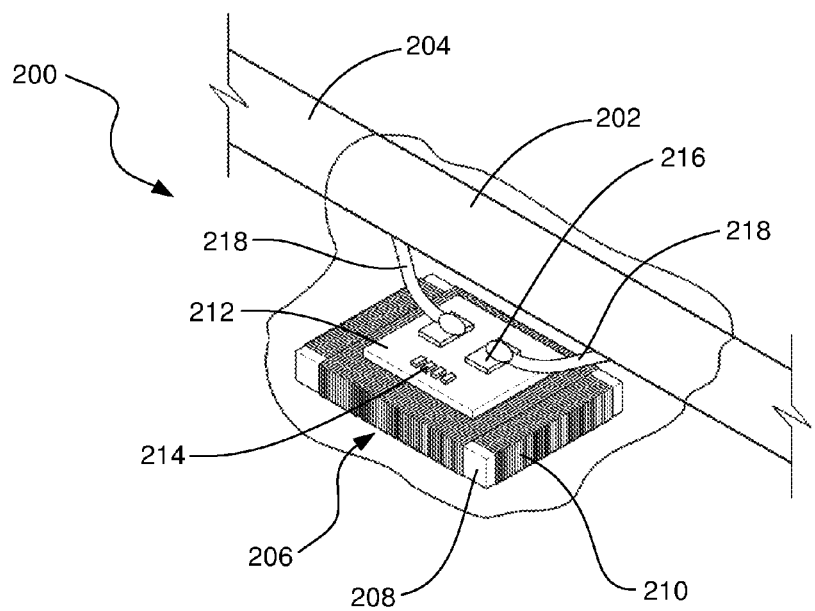
FIG. 4 is a close-up perspective view of an embodiment of a combined charging and communications element attached to a lead of an implantable device, the element having a generally flat, rectangular coil.

The control elements can be configured in a variety of ways. Close-up perspective views of several embodiments of charging and communications elements are shown in FIGS. 4-8. Shown in FIG. 4 is a combined charging and communications element 200 attached to a lead 202 of an implantable device (not shown). The lead includes a protective sheath 204 surrounding the lead and the control element 200, which is partially stripped away in this view to expose the control element. The element 200 has a generally flat, rectangular shape, with a coil 206 comprising a generally flat, rectangular ferromagnetic core 208 wrapped with electrically conductive windings 210. The coil 206 is attached to a substrate 212, which can be a silicon circuit board with circuitry 214 provided thereon. The substrate also includes contact pads 216 for connection of wires 218 that connect the control element 200 to the lead 202.

The control element 200 of FIG. 4 can function as either or both a recharging element and an antenna. When functioning as a recharging element, an alternating electric field in close proximity to the coil 206 will induce current in the coil. The circuitry 214 that is provided as part of the control element 200 can include a full wave rectifier circuit for converting AC to DC, and this current is then transmitted back to the controller (not shown) via the wires 218 for recharging of the batteries. For communications, the coil 206 can function as an antenna. In this case the circuitry 214 that is provided as part of the control element 200 can include filter circuitry, and again, the communications signals can be transmitted to the controller via the wires 218.

Figure 5:
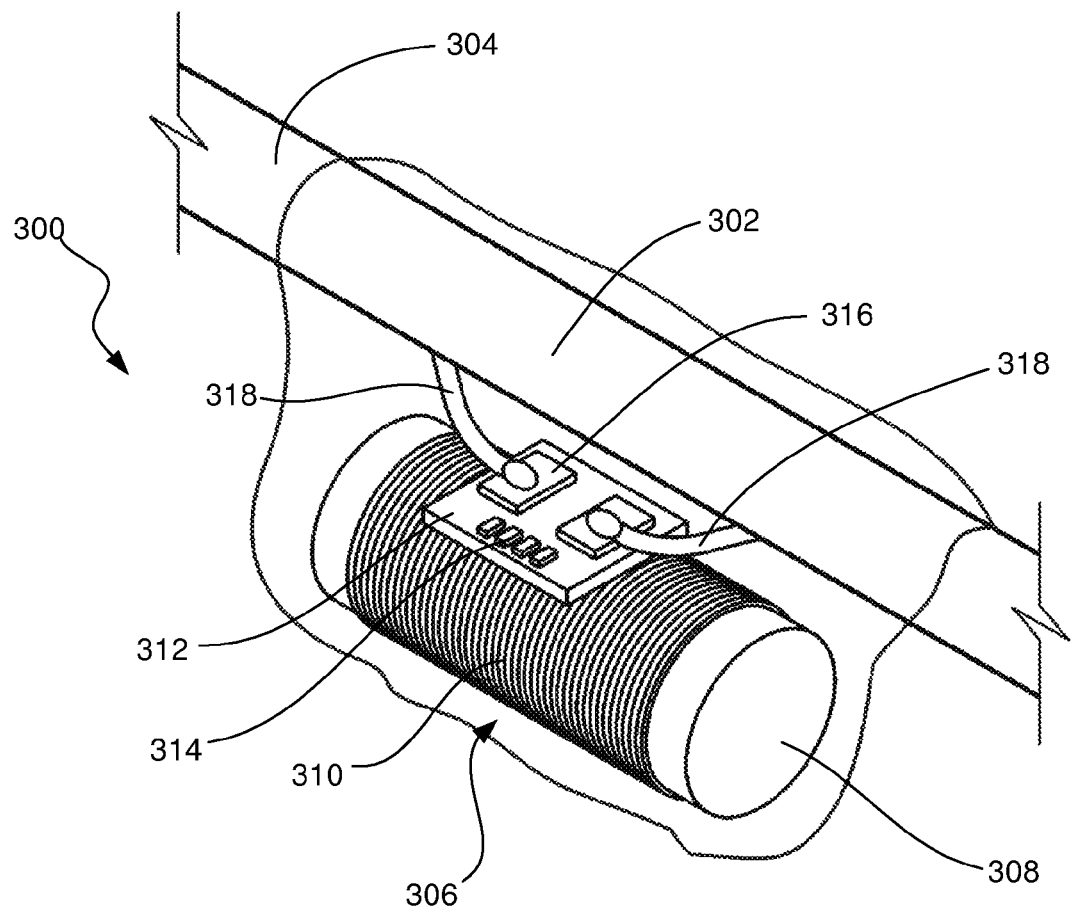
FIG. 5 is a close-up perspective view of another embodiment of a combined charging and communications element attached to a lead of an implantable device, the element having a cylindrical coil.

The control elements can have a variety of configurations. Shown in FIG. 5 is a close-up perspective view of another embodiment of a combined charging and communications element 300 attached to a lead 302 of an implantable device. Again, the lead and the control element are encased in a sheath 304 that is partially stripped away in this view. In this embodiment the control element has a cylindrical coil 306, with a cylindrical ferromagnetic core 308 wrapped by electrical windings 310. The attached substrate 312 can include circuitry 314 including rectifier circuitry for AC to DC conversion, and/or filter circuitry for communications, as well as contact pads 316 for connection of wires 318 that connect the control element 300 to the lead 302.

Figure 6:
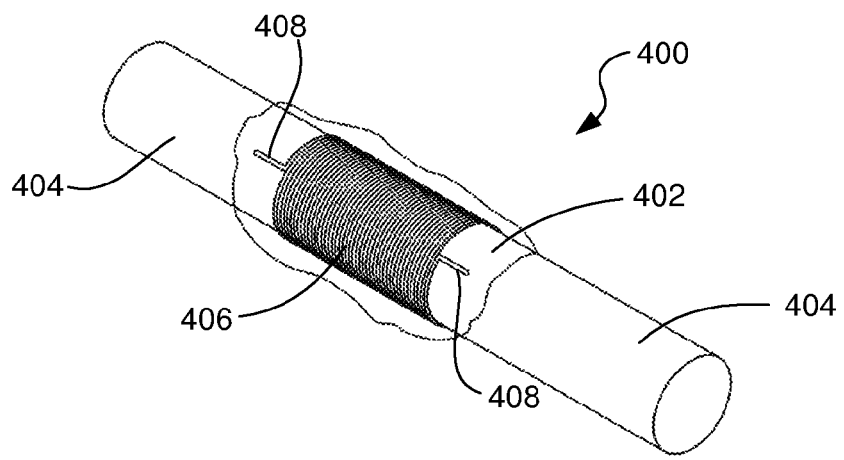
FIG. 6 is a close-up perspective view of another embodiment of a combined charging and communications element associated with a lead of an implantable device, the element having a cylindrical coil wrapped around the lead.

While the embodiments of FIGS. 4 and 5 include a power and/or communications circuit attached to the coil outside of the lead, different configurations can also be used. For example, shown in FIG. 6 is a close-up perspective view of another embodiment of a combined charging and communications element 400, with a portion of the sheath 404 surrounding the lead 402 stripped away. In this embodiment, the control element is a cylindrical coil 406 comprising electrical windings wrapped around the lead itself. The ends 408 of the coil extend into the lead for connection to the appropriate wires therein. Since it wraps around the lead rather than a ferromagnetic core, it will be apparent that the coil 406 will have a lower inductance than a comparable coil having a ferromagnetic core. However, those of skill in the art will recognize that the inductance of this coil can be increased by providing a greater number of windings. A power rectifier circuit and/or communications filter circuit (not shown) can be included inside the lead 404, such as in the center of the coil 406 (since there is no metal core).

Alternatively, power and/or communications circuitry (not shown) for the control element 400 of FIG. 6 can be separated from the charging and/or communications element, and instead associated with the controller of the implantable device (60 in FIG. 2). This embodiment is illustrated in FIG. 2, wherein a circuit board 78 is included in the controller 60. In this way, one rectifier circuit and one communications filter circuit can be used for all control elements along the lead, and this circuitry can be combined with the control circuitry of the controller (e.g. the pulse generation device). Indeed, while power and/or communications circuitry is shown associated with the control element in each of the embodiments of FIGS. 5-6 and 7-8, this circuitry can instead be associated with the controller in the same way, and the substrates in these embodiments need not include separate circuitry, but can be primarily for mechanical attachment of the coil to the lead.

Figure 7:
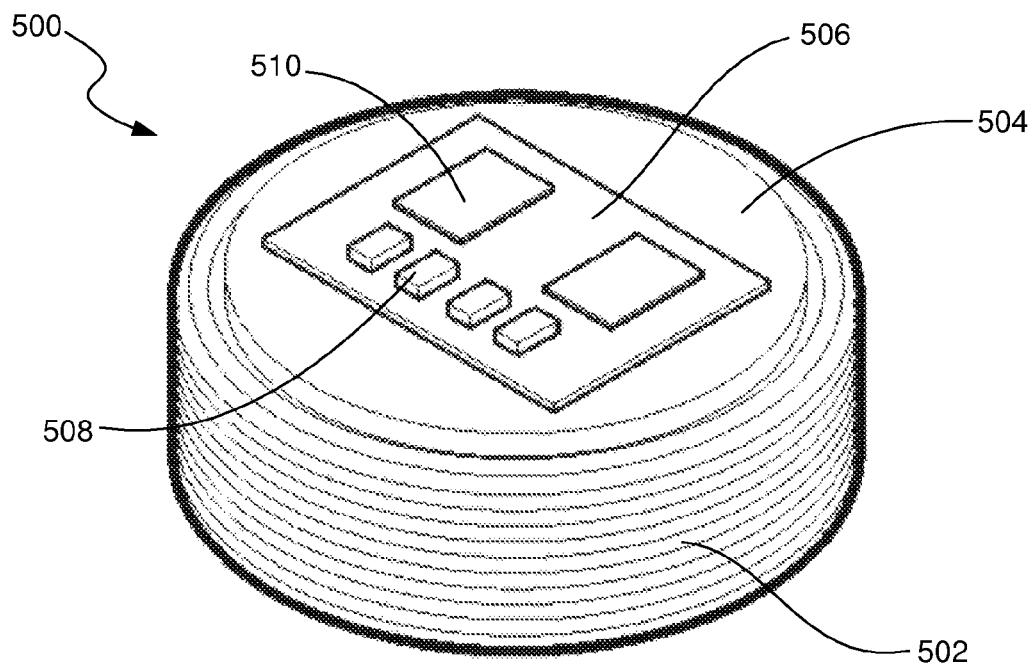
FIG. 7 is a close-up perspective view of another embodiment of a combined charging and communications element that can be attached to a lead of an implantable device, the element having a coil wrapped around a generally flat, cylindrical core.
Figure 8:
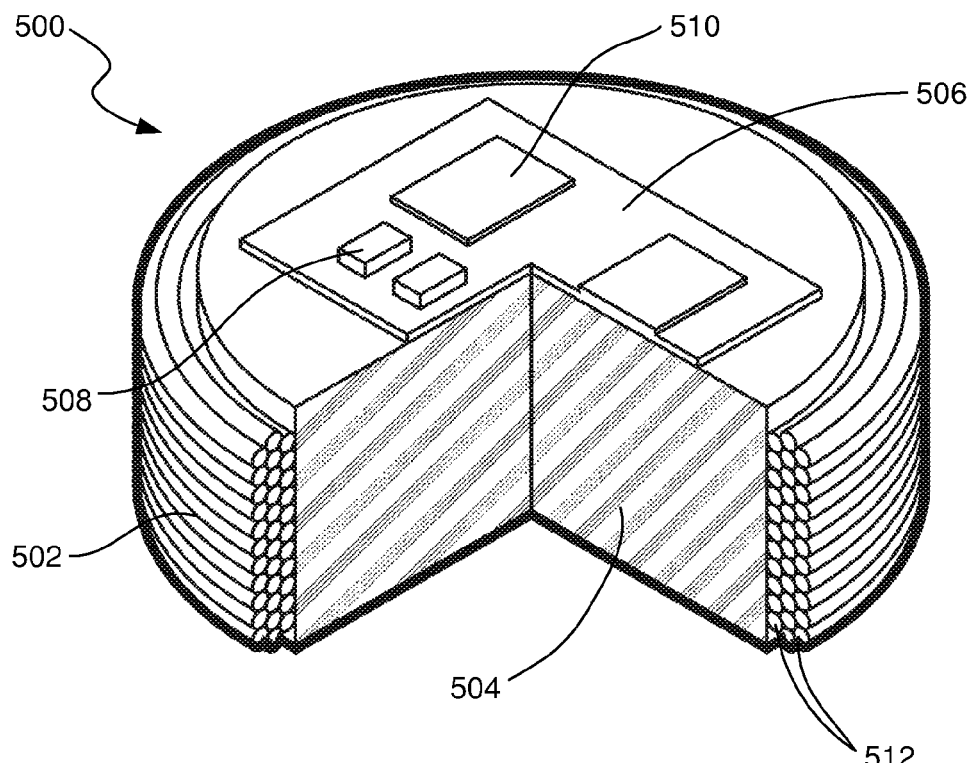
FIG. 8 is a partial cross-sectional view of the charging and communications element of FIG. 7.

FIGS. 7 and 8 provide close-up perspective views of another embodiment of a combined charging and communications element 500 that can be attached to a lead of an implantable device. In these figures the lead is not shown, but this element can be attached to a lead in the same way as the control elements shown in FIGS. 4-5. This element includes a coil of windings 502 wrapped around a generally flat, cylindrical ferromagnetic core 504. A substrate 506 with circuitry 508 can be attached to a top surface of the core, with contact pads 510 for connecting wires (not shown) to the associated lead (not shown). The partial cross-sectional view of FIG. 8 shows the core 504 of the coil, and shows that the coil 502 can include multiple layers 512 of windings. Indeed, any of the embodiments shown in FIGS. 5-9 can include multiple layers of windings to provide a desired level of inductance. Higher inductance will tend to increase the power transfer capacity of the coil, and more windings will also tend to provide greater sensitivity when the coil functions as an antenna.

It is to be understood that the control element embodiments shown in FIGS. 4-8 are exemplary only, and that other configurations can be used. Power and/or communications circuitry can be included with each control element, or circuitry can be included only in the controller of the implantable device as a whole. Individual wires can extend to each control element, or the control elements can be attached in series along a single set of wires in the lead. The size of the control elements can also vary. The inventors believe that for any of the embodiments in FIGS. 4-8 a maximum dimension of about 11 mm for the control element is desirable. More particularly, control elements having a maximum dimension of 5 mm to 10 mm are believed to be desirable. However, control elements that are larger or smaller than this size or size range can also be used.

Additionally, the placement and function of the control elements along the lead can vary. Referring to FIG. 2, the inventors believe that a desirable spacing of control elements 56 along the lead 54 is from 1 cm to 5 cm, though other spacings can also be used. It will be apparent that a closer spacing of control elements can provide greater communications and recharging benefits, but will tend to increase the cost and bulk of the lead. In one embodiment, a lead of 35 cm length is provided with 35 control elements, spaced at about 1 cm along the lead. Alternatively, the spacing of the control elements can be non-uniform. For example, referring to FIG. 2, for a vagus nerve stimulation device, the spacing of control elements can be closer near the electrodes 62, in the neck region 80, where there is less fatty tissue.

Additionally, the control elements 56 can have different functions. For example, some of the control elements can be communication elements only, while others are charging elements only. In one embodiment, the lead can include an array of alternating charging and communication elements. This configuration can provide certain desirable features. For example, since communication elements can be smaller than recharging elements, this allows the overall bulk of the lead to be reduced, and can also reduce its cost.

The lead for an implantable device disclosed herein thus provides a number of desirable features. It addresses the challenges associated with recharging and communicating with an implanted electronic device, and can be associated with a variety of different implantable devices, such as VNS systems, heart pacemakers or defibrillation devices, implantable drug delivery devices, etc. The device locates the charging and communication elements, which would typically otherwise be housed within the implanted electronic device, into a lead. The communication and recharging elements can be of any shape or size as needed by each function, and individual elements can be configured to function as both a recharging or communication element. By providing multiple control elements in the lead, the recharging ability and potentially also recharging speed are enhanced, as is the ability to communicate with the implanted electrical device. This configuration also eliminates or significantly reduces the "skin effect" caused by the metal casing of the pulse generator that shields the elements within the generator from the oscillating magnetic field. For this reason, more power is required by the external recharger to recharge batteries when the receiving element is inside the pulse generator casing, and heating of the pulse generator casing may be reduced because the recharging elements are outside that casing.

Although various embodiments have been shown and described, the invention is not so limited and will be understood to include all such modifications and variations as would be apparent to one skilled in the art. For example, equivalent elements may be substituted for those specifically shown and described, certain features may be used independently of other features, and the number and configuration of various components described above may be altered, all without departing from the spirit or scope of the invention as defined in the appended claims.

Such adaptations and modifications should and are intended to be comprehended within the meaning and range of equivalents of the disclosed exemplary embodiments. It is to be understood that the phraseology of terminology employed herein is for the purpose of description and not of limitation. Accordingly, the foregoing description of the exemplary embodiments of the invention, as set forth above, are intended to be illustrative, not limiting. Various changes, modifications, and/or adaptations may be made without departing from the spirit and scope of this invention.

What is claimed is:

1. A lead for an implantable medical device (IMD), the lead comprising:
   a flexible, implantable tether that is electrically connectable to an IMD; and
   two or more control elements, disposed at separate locations along a length of the tether, wherein each of the two or more control elements is electrically interconnectable to the IMD and is configured to transmit power signals, communication signals, or both, to the IMD,
   wherein at least one of the two or more control elements includes a coil, wherein the coil includes a ferromagnetic core and is configured to generate an electrical current in response to a changing electrical field, and wherein the electrical current is at least one source of the power signals.

2. The lead of claim 1, wherein a first particular control element of the two or more control elements is configured to transmit the communication signals to the IMD, and wherein a second particular control element of the two or more control elements is configured to transmit the power signals to the IMD.

3. The lead of claim 2, wherein the first particular control element includes an antenna that is configured to communicate with a wireless communication device by transmitting and receiving the communication signals.

4. The lead of claim 1, wherein a particular control element of the two or more control elements is configured to transmit the communication signals to the IMD and is configured to transmit the power signals to the IMD.

5. The lead of claim 1, wherein the coil is further configured to communicate with a wireless communication device.

6. The lead of claim 5, wherein a particular control element of the two or more control elements includes the coil, and wherein the particular control element includes a communications filter circuit electrically connected to the coil.

7. The lead of claim 5, wherein a particular control element of the two or more control elements includes the coil, and wherein the particular control element includes a power rectifier circuit that is coupled to the coil.

8. The lead of claim 1, wherein the tether is configured to be implanted into a patient body at a first depth that is less than second depth at which the IMD is implanted into the patient body.

9. The lead of claim 1, wherein the two or more control elements are disposed along the length of the tether based on an order that alternates between first particular control elements that transmit the power signals and second particular control elements that transmit the communication signals.

10. The lead of claim 1, wherein each of the two or more control elements is electrically connected to the IMD via a wire that is distinct to a particular control element.

11. The lead of claim 1, wherein a distance between a pair of adjacent control elements of the two or more control elements is at least 1 centimeter.

12. A system comprising:
an implantable medical device (IMD) comprising a programmable device and a rechargeable battery; and
a lead of the IMD comprising:
a flexible, implantable tether, electrically connected to the IMD; and
two or more control elements, disposed at separate locations along a length of the tether, wherein the two or more control elements are configured to transmit power signals, communication signals, or both, to the IMD; and
wherein at least one of the two or more control elements includes a coil, wherein the coil includes a ferromagnetic core and is configured to generate an electrical current in response to a changing electrical field, and wherein the electrical current is at least one source of the power signals.

13. The system of claim 12, wherein a particular control element of the two or more control elements includes the coil, wherein the particular control element includes a power rectifier circuit configured to convert the electrical current into a direct current to generate the power signals.

14. The system of claim 13, wherein a second particular control element of the two or more control elements includes an antenna that is configured to wirelessly communicate with the programmable device and an external communication device located outside a patient body in which the IMD is implanted.

15. The system of claim 12, wherein the rechargeable battery is charged responsive to the power signals.

16. The system of claim 12, wherein the two or more control elements are disposed along the length of the tether based on an order that alternates between first particular control elements that transmit the power signals and second particular control elements that transmit the communication signals.

17. The system of claim 12, wherein the tether is configured to be implanted into a patient body at a first depth that is less than second depth at which the IMD is implanted into the patient body.

18. The system of claim 12, further comprising an electrode that is disposed at a distal end of the tether and attached to a nerve of a patient body in which the IMD is implanted, wherein the programmable device further comprises a pulse generation device to deliver electrical stimulation to the nerve via the electrode.

19. The system of claim 12, wherein the changing electrical field is produced by a recharging device that is positioned at a location outside a body of a patient in which the IMD is implanted, and wherein the location is proximate to a region in the body of the patient where the tether is located.

20. A vagus nerve stimulation system comprising:
an implantable, programmable pulse generation device including a rechargeable battery;
an implantable electrode that is attachable to a vagus nerve within a body of a patient;
a flexible, implantable tether that electrically connects to the implantable, programmable pulse generation device and the implantable electrode; and
two or more control elements, disposed at separate locations along a length of the tether, wherein each of the two or more control elements is configured to transmit power signals, communication signals, or both, to the implantable, programmable pulse generation device,
wherein at least one of the two or more control elements includes a coil, wherein the coil includes a ferromagnetic core and is configured to generate an electrical current in response to a changing electrical field, and wherein the electrical current is at least one source of the power signals.

21. The system of claim 20, wherein a first control element of the two or more control elements includes the coil and is distinct from a second control element of the two or more control elements, the second control element including a second coil, wherein the second coil includes a second ferromagnetic core and is configured to generate a second electrical current in response to the changing electrical field, wherein the second control element transmits the power signals, and wherein the second electrical current is a second source of the power signals.

22. The system of claim 21, wherein the rechargeable battery is charged using the power signals.

* * * * *